United States Patent
De Rose et al.

(10) Patent No.: US 10,400,197 B2
(45) Date of Patent: Sep. 3, 2019

(54) DETERGENT COMPOSITIONS WITH LIPASE AND BIOSURFACTANT

(71) Applicant: Conopco, Inc., Englewood Cliffs, NJ (US)

(72) Inventors: Simone Antonio De Rose, Exeter (GB); Dietmar Andreas Lang, Liverpool (GB); Jennifer Ann Littlechild-Bond, Tiverton (GB); Halina Rose Novak, Merelbeke (BE); Sukriti Singh, Wirral (GB)

(73) Assignee: CONOPCO INC., Englewood Cliffs, NJ (US)

( * ) Notice: Subject to any disclaimer, the term of this patent is extended or adjusted under 35 U.S.C. 154(b) by 0 days.

(21) Appl. No.: 15/753,446

(22) PCT Filed: Aug. 25, 2016

(86) PCT No.: PCT/EP2016/070048
§ 371 (c)(1),
(2) Date: Feb. 19, 2018

(87) PCT Pub. No.: WO2017/036902
PCT Pub. Date: Mar. 9, 2017

(65) Prior Publication Data
US 2018/0245024 A1    Aug. 30, 2018

(30) Foreign Application Priority Data

Aug. 28, 2015 (EP) ..................... 15183065

(51) Int. Cl.
| | |
|---|---|
| *C12N 9/20* | (2006.01) |
| *C11D 3/386* | (2006.01) |
| *C11D 1/66* | (2006.01) |
| *C11D 1/83* | (2006.01) |
| *C11D 11/00* | (2006.01) |
| *C11D 1/22* | (2006.01) |
| *C11D 1/29* | (2006.01) |

(52) U.S. Cl.
CPC ......... *C11D 3/38627* (2013.01); *C11D 1/662* (2013.01); *C11D 1/83* (2013.01); *C11D 11/0017* (2013.01); *C12N 9/20* (2013.01); *C11D 1/22* (2013.01); *C11D 1/29* (2013.01)

(58) Field of Classification Search
None
See application file for complete search history.

(56) References Cited

U.S. PATENT DOCUMENTS

2011/0201536 A1    8/2011    O'Connell et al.

FOREIGN PATENT DOCUMENTS

| WO | WO2012010406 | 1/2012 | |
|---|---|---|---|
| WO | WO2012010407 | 1/2012 | |
| WO | WO-2013024143 A1 * | 2/2013 | ............. C11D 3/386 |
| WO | WO2013037643 | 3/2013 | |

OTHER PUBLICATIONS

Studer. Residue mutations and their impact on protein structure and function: detecting beneficial and pathogenic changes. Residue mutations and their impact on protein structure and function: detecting beneficial and pathogenic changes. Biochem. J. (2013) 449, 581-594.*
Lipase, Database Accession No. AISw03, Database UniProt, 2007, p. 1, (XP002764274).
Feller et al., Lipases from psychrotrophic antarctic bacteria, FEMS Microbiology Letters, 1990, pp. 239-244, vol. 66 No. 1-3.
Riley et al., Genomics of an extremem pschrophile, Psychromonas ingrahamii, BMC Genomoics, May 6, 2008, p. 210, vol. 9, No. 1.
Search Report and Written Opinion in EP15183065, dated Feb. 17, 2016.
Search Report and Written Opinion in PCTEP2016070047, dated Nov. 25, 2016.
Search Report and Written Opinion in PCTEP2016070048, dated Nov. 22, 2016.

* cited by examiner

*Primary Examiner* — Yong D Pak
(74) *Attorney, Agent, or Firm* — Foley & Lardner LLP

(57) ABSTRACT

Compositions comprising lipases and biosurfactants, especially psychrophilic lipases and biosurfactants.

10 Claims, 6 Drawing Sheets

Specification includes a Sequence Listing.

DETERGENT COMPOSITIONS WITH LIPASE AND BIOSURFACTANT

This application claims priority benefit of EP15183065.0 filed 28 Aug. 2015, the contents of which are incorporated herein in their entirety.

The invention relates to compositions comprising lipases and biosurfactants, especially psychrophilic lipases and biosurfactants.

Laundry compositions often contain enzymes to improve cleaning performance. However, many enzymes are activated only at higher temperatures, which means that large volumes of water must be heated to provide a wash liquor at an appropriate temperature to activate the enzyme content.

This is proving increasingly unpopular as consumers and laundry composition providers focus on sustainability, and as energy prices rise.

However, despite the obvious appeal of low temperature and cold washes, consumers are often unwilling or reluctant to sacrifice cleaning performance.

There is a need in the art for laundry compositions having improved cleaning performance at low temperatures.

SUMMARY

The invention relates to compositions comprising lipases and biosurfactants. Biosurfactants, including certain preferred biosurfactants, are described here, as are certain preferred ratios of lipase to biosurfactant. A preferred biosurfactant is mannosylerythritol lipid (MEL), preferably mannosylerythritol lipid enriched in MEL-B.

Suitably, the lipase is a psychrophilic lipase, for example a cold adapted lipase from *Pyschromonas ingrahamii*. In other words, suitably the lipase is a *Psychromonas ingrahamii* lipase. The inventors have identified a putative class 3 lipase from *P. ingrahamii* termed PinLip. An amino acid sequence alignment is shown in FIG. 1 (aligned with Lipex). The Lipex sequence displayed therein may be considered SEQ. ID1., while the PinLip sequence shown therein may be considered SEQ. ID2.

As used herein, the term "psychrophilic" enzyme refers to an enzyme that is effective at a temperature of 0° C. to 25° C.

Accordingly, the invention further relates to a lipase having an amino acid sequence as shown in FIG. 1 (labelled Pin-Lip), or a sequence identity of at least 70% with the amino acid sequence as shown in FIG. 1. Alternatively, this identity may be any of 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100% sequence identity.

Cold active enzymes are desirable as cooler wash liquor temperatures may be used. This in turn improves sustainability (as heating water for laundry is a major source of $CO_2$) and reduces consumer energy bills. This is also useful for laundering articles that may suffer as a result of high temperature washing, for example by shrinking or fading.

However, a major problem with cold active enzymes is maintaining enzyme stability, especially in liquid formulations, during storage, and subsequently during the wash cycle. Furthermore, cold wash cycles are typically not suitable for certain stain types, in particular fat stains.

The invention seeks to address at least some of these problems.

In a first aspect, the invention may provide a composition comprising a psychrophilic lipase and a biosurfactant.

The inventors have shown that the inclusion of a biosurfactant improves cleaning when compared to the psychrophilic lipase alone. The inventors have also shown that the combination of psychrophilic lipase and biosurfactant is, in at least some cases, superior to a combination of the benchmark mesophilic lipase Lipex and the same biosurfactants, in particular at lower temperatures.

In some cases, the psychrophilic lipase a *Psychromonas ingrahamii* lipase. The lipase may be wild-type or mutant. The lipase may have an amino acid sequence as shown in FIG. 1 (labelled Pin-Lip), or a sequence identity of at least 70% with the amino acid sequence as shown in FIG. 1. Alternatively, this identity may be any of 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100% sequence identity.

Preferably, the composition is a liquid. Liquid compositions are preferred by many consumers, and concentrated liquid products improve sustainability owing to decreased packaging and a smaller transportation footprint.

Suitably, the biosurfactant is a glycolipid (in other words, the biosurfactant comprises a carbohydrate). Suitable biosurfactants are as described herein and include rhamnolipid, sophorolipid, trehalolipid (trehalose lipids), and a mannosylerythritol lipid (MEL), and combinations thereof.

It will be appreciated that each of these terms refers to a known class of compounds. The glycolipid may be of a single structure, for example, MEL-B, or it may be a mixture of structures within the class.

In some cases, the biosurfactant is a rhamnolipid. The rhamnolipid may comprise at least 50 wt. % monorhamnoplipid, optionally at least 60 wt. %, 70 wt. %, 80 wt. %, 90 wt. %, 95 wt. %, 98 wt. %, even up to 100 wt. %. The rhamnolipid may comprise at least 50 wt. % di-rhamnolipid, optionally at least 60 wt. %, 70 wt. %, 80 wt. %, 90 wt. %, 95 wt. %, 98 wt. %, even up to 100 wt. %. Preferably, the rhamnolipid is enriched in monorhamnolipid. For example, the rhamnolipid may comprise at least 50 wt. % monorhamnolipid, for example at least 80 wt. % monorhamnolipid. The biosurfactant may be exclusively monorhamnolipid.

In some cases, the biosurfactant is a mannosylerythritol lipid. Preferably, the mannosylerythritol lipid in enriched in mannosylerythritol lipid B (MEL-B). The MEL may comprises at least 50 wt. % MEL-B, optionally at least 60 wt. %, 70 wt. %, 80 wt. %, 90 wt. %, 95 wt. %, 98 wt. %, even up to 100 wt. %. The biosurfactant may be exclusively MEL-B.

The inventors have observed that compositions comprising a psychrophilic lipase as described herein and a biosurfactant provide enhanced cleaning at lower total surfactancy when compared to the benchmark enzyme Lipex and a biosurfactant.

In some cases, the total surfactant content of the composition is 30 wt. % or less, for example, 25% or less, 20% or less, 18% or less, 15% or less, 12% or less or even lower.

It will be appreciated that surfactants other than biosurfactants may be present in the compositions. In other words, the composition may comprise glycolipid surfactants and other surfactants. In some cases, the total surfactant content is glycolipid surfactant content. In other cases, there is a mixture of glycolipid surfactant and other surfactant.

In some cases, the ratio of biosurfactant to non-biosurfactant is from 1:9 to 1:1, for example, from 1:9 to 1:2, from 1:9 to 1:3, from 1:9 to 1:4.

In other words, the biosurfactant content may be from 1 to 100 wt. % of the total surfactant content of the composition. In some cases, the biosurfactant content is from 1 to 50 wt. % of the total surfactant content of the composition, for example, from 10 to 50 wt. % of the total surfactant content of the composition. In some cases it is 10 wt. %, 20 wt. %, 30 wt. %, 40 wt. %, or 50 wt. %.

The non-biosurfactants (other surfactants) may include, without limitation LAS (linear alkylbenzene sulfonate), SLES (sodium lauryl ether sulfate), and NI (non-ionic surfactants). For example, in some cases the ratio of LAS to SLES to NI is 2:1:3.

Suitably, the ratio of lipase to biosurfactant is from 1:10 to 1:200, for example, from 1:10 to 1:150, from 1:10 to 1:100, from 1:15 to 1:80, from 1:20 to 1:60, from 1:30 to 1:50. In some cases, it is around 1:40.

The compositions of the invention permit articles (such as clothes, curtains, household linen, and towels) to be laundered at lower temperatures.

In a second aspect, the invention may provide a composition comprising a lipase and a mannosylerythritol lipid. Preferably, the mannosylerythritol lipid in enriched in mannosylerythritol lipid B (MEL-B). The MEL may comprises at least 50 wt. % MEL-B, optionally at least 60 wt. %, 70 wt. %, 80 wt. %, 90 wt. %, 95 wt. %, 98 wt. %, even up to 100 wt. %. The biosurfactant may be exclusively MEL-B. Except where expressly provided otherwise, the preferences described with respect to the first aspect also apply to the second aspect.

Accordingly, in a further aspect, the present invention relates to a method of laundering articles, the method comprising washing articles in an aqueous wash liquor containing a composition according to the first aspect or second aspect. For example, the temperature of the water is room temperature (also referred to as ambient temperature).

Advantageously, cooler washing steps may be used owing to the desirable stain removal and cleaning at low temperatures facilitated combination of the invention. For example, even for fat staining, the washing step temperature may be 40° C. or less, 35° C. or less, 30° C. or less, 25° C. or less. In some preferred embodiments, no heating is used (unheated water is used): the wash liquor temperature is the temperature of the cold fill into the machine or from the faucet into a bowl or basin. Naturally, this will vary with supply and geographical variation, but may be as low as 10° C., or even lower. For example, in northern US states the water supply may be as low as 7° C. or even 5° C. in winter. This may be referred to as an ambient wash.

Not heating the water reduces energy consumption, reducing energy bills and making laundry more environmentally friendly.

Accordingly, in a further aspect, the invention provides a method of laundering articles, the method comprising washing articles in an aqueous wash liquor containing a composition according to the first aspect or second aspect, wherein the temperature of the wash liquor is 25° C. or less, 20° C. or less, 15° C. or less, 10° C. or less, or even 5° C. or less.

The inventors have found that for at least some psychrophilic enzymes such as PinLip, the activity for certain short/medium length esters improves at the upper temperature range of such an ambient wash. Accordingly, in some cases, the temperature of the wash liquor is 15-25° C.

However, the inventors have observed that across a wide variety of temperature ranges, the lipase is active for a range of ester chain lengths.

The inventors have found that low concentrations of psychrophilic lipase may be used. For example, the concentration of psychrophilic lipase in the wash liquor may be 2.5 to 20 mg/L.

This further improves sustainability and economy.

Suitably, the concentration of biosurfactant in the wash liquor is 0.001 to 1 wt %, preferably 0.005 to 0.5 wt %, 0.01 to 0.5 wt %, 0.01 to 0.2 wt %.

DRAWINGS

DESCRIPTION

Abbreviations

Suc-Ala-Ala-Phe-7-amido-4-methyl coumarin-N-SUCCINYL-L-ALANYL-L-ALANYL-L-PHENYLALANINE-4-METHYL-COUMARYL-7-AMIDE CAPS—N-cyclohexyl-3-aminopropanesulfonic acid Tris-tris(hydroxymethyl)aminomethane CIE—'Commission Internationale de l'Eclairage'

SRI—Stain Removal Index

Definitions

As used herein the term "effective" means that the enzyme has the ability to achieve stain removal or catalytic capability (in the given temperature zone).

As used herein the term "treatment" in the context of enzymatic fabric treatment composition preferably means cleaning and more preferably stain removal.

Preferably stain removal is measured in terms of Remission units or a Remission index. Effective stain removal is preferably represented by remission equal to or greater than 2 Remission units.

Enzymes

As used herein the term "enzyme" includes enzyme variants (produced, for example, by recombinant techniques). Examples of such enzyme variants are disclosed, e.g., in EP 0251446 (Genencor), WO 91/00345 (Novo Nordisk), EP 0525610 (Solvay) and WO 94/02618 (Gist-Brocades NV), each of which is incorporated by reference in its entirety.

Enzymes may be from bacterial or fungal origin. Chemically modified or protein engineered mutants are included.

Percentage Sequence Identity

Percentage (%) sequence identity is defined as the percentage of amino acid residues in a candidate sequence that are identical with residues in the given listed sequence (referred to by the SEQ ID No.) after aligning the sequences and introducing gaps if necessary, to achieve the maximum sequence identity, and not considering any conservative substitutions as part of the sequence identity. Sequence identity is preferably calculated over the entire length of the respective sequences.

Where the aligned sequences are of different length, sequence identity of the shorter comparison sequence may be determined over the entire length of the longer given sequence or, where the comparison sequence is longer than the given sequence, sequence identity of the comparison sequence may be determined over the entire length of the shorter given sequence.

For example, where a given sequence comprises 100 amino acids and the candidate sequence comprises 10 amino acids, the candidate sequence can only have a maximum identity of 10% to the entire length of the given sequence. This is further illustrated in the following example:

```
(A)
Given seq:
    XXXXXXXXXXXXXXX (15 amino acids)

Comparison seq:
    XXXXXYYYYYYY (12 amino acids)
```

Figures 1, 2:
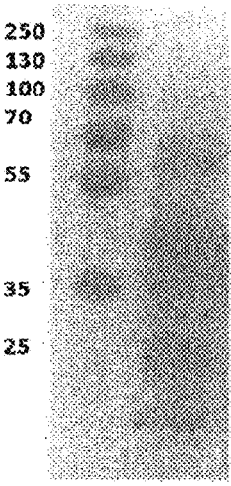
FIG. 1 shows the sequence alignment of a putative class 3 lipase from *P. ingrahammii*.
FIG. 2 shows a 10% SDS-PAGE gel of purified PinLip.

The given sequence may, for example, be that encoding Pin Lip as shown in FIG. 1.

% sequence identity=the number of identically matching amino acid residues after alignment divided by the total number of amino acid residues in the longer given sequence, i.e. (5 divided by 15)×100=33.3%

Where the comparison sequence is longer than the given sequence, sequence identity may be determined over the entire length of the given sequence. For example:

```
(B)
Given seq:
    XXXXXXXXXX (10 amino acids)

Comparison seq:
    XXXXXYYYYYYZZYZZZZZZ (20 amino acids)
```

Again, the given sequence may, for example, be that encoding Pin Lip as shown in FIG. 1.

% sequence identity=number of identical amino acids after alignment divided by total number of amino acid residues in the given sequence, i.e. (5 divided by 10)×100=50%.

Alignment for purposes of determining percent amino acid sequence identity can be achieved in various ways known to a person of skill in the art, for instance, using publicly available computer software such as ClustalW 1.82. T-coffee or Megalign (DNASTAR) software. When using such software, the default parameters, e.g. for gap penalty and extension penalty, are preferably used. The default parameters of ClustalW 1.82 are: Protein Gap Open Penalty=10.0, Protein Gap Extension Penalty=0.2, Protein matrix=Gonnet, Protein/DNA ENDGAP=-1, Protein/DNA GAPDIST=4.

Identity of nucleic acid sequences may be determined in a similar manner involving aligning the sequences and introducing gaps if necessary, to achieve the maximum sequence identity, and calculating sequence identity over the entire length of the respective sequences. Where the aligned sequences are of different length, sequence identity may be determined as described above and illustrated in examples (A) and (B).

Psychrophilic Enzymes

As used herein the term "psychrophilic enzyme" means enzymes that are effective at a temperature of 0° C.-25° C.

As used herein the term "effective" means that the enzyme has the ability to achieve stain removal or catalytic capability (in the given temperature zone).

Preferably stain removal is measured in terms of Remission units or a Remission index. Effective stain removal is preferably represented by remission equal to or greater than 2 Remission units.

In some cases, the psychrophilic enzyme is effective at a temperature of 0° C.-20° C., for example at a temperature of 0° C.-15° C. In some cases, the psychrophilic enzyme is effective at a temperature of 0° C.-10° C.

Preferably the psychrophilic enzyme comprises e.g. a lipase and/or a phospholipase.

Lipases are highly advantageous psychrophilic enzymes because fats and oil based stains are more difficult to remove at psychrophilic temperatures. Phospholipases are advantageous psychrophilic enzymes for much the same reason.

Psychrophilic lipases include lipases from *Acinetobacter* sp. Strain No. 6 (Suzuki et al. (2001) J. Biosci. Bioeng. 92: 144-148); *Acinetobacter* sp. Strain No. 016 (Brueuil and Kushner, (1975) Can. J. Microbiol. 21:423-433); *Achromobacter lipolyticum* (Khan et al., (1967), Biochem. Biophys. Acta. 132:68-77 1967), *Aeromonas* sp. Strain No. LPB 4 (Lee et al. (2003), J. Microbiol. 41:22-27), *Aeromonas hydrophila* (Pemberton et al. (1997) FEMS Microbiol. Lett. 152:1-10); *Bacillus sphaericus* MTCC 7526 (Joseph. PhD Thesis (2006) Allahabad Agricultural Institute, Allahabad, Ind.); Microbacterium phyllosphaerae MTCC 7530, *Moraxella* sp. (Feller et al. (1990) FEMS Microbiol. Lett. 66:239-244; *Moraxella* sp. TA144 (Feller et al. (1991) Gene.102: 111-115); *Photobacterium lipolyticum* M37 (Ryu et al. (2006) Appl. Microbiol. Biotechnol. 70: 321-326); *Pseudoalteromonas* sp. Wp27 (Zeng et al. (2004) J. Microbiol. Biotechnol. 14: 952-958); *Pseudoalteromonas* sp. (Giudice et al. (2006) J. Applied Microbiology 101:1039-1048), *Psychrobacter* sp. and *Vibrio* sp.; *Psychrobacter* sp. Wp37 (Zeng et al. (2004) J. Microbiol. Biotechnol. 14: 952-958); *Psychrobacter okhotskensis* sp. (Yumoto et al. (2003) Int. J. Syst. Evol. Microbiol. 53: 1985-1989); *Psychrobacter* sp. Ant300 (Kulakovaa et al. (2004) Biochemica. Biophysica. Acta. 1696:59-65); *Psychrobacter immobilis* strain B 10 (Arpigny et al. (1997) J. Mol. Catal. B Enzy. 3: 29-35.), *Psychromonas ingrahamii* (Gosink et al. (1993) FEMS Microbiol Ecol 102, 85-90; *Serratia marcescens* (Abdou, (2003) J. Dairy Sci. 86:127-132), *Staphylococcus aureus* (Alford and Pierce, (1961) J. Food Sci. 26:518-524), and *Staphylococcus epidermidis* (Joseph et al. (2006) J. Gen. Appl. Microbiol. 52: 315-320). Each document is incorporated by reference in its entirety for all purposes, but in particular the disclosure of psychrophilic enzyme identity, structure, reactivity and methods of obtaining said enzymes.

Preferably, the psychrophilic lipase is a class 3 lipase from *Psychromonas ingrahamii* (known as PinLip).

Mesophilic Lipases

Exemplary mesophilic lipases include lipases from *Humicola* (synonym *Thermomyces*), e.g. from *H. lanuginosa* (*T. lanuginosus*) or from *H. insolens*, a *Pseudomonas* lipase, e.g. from *P. alcaligenes* or *P. pseudoalcaligenes, P. cepacia, P. stutzeri, P. fluorescens, Pseudomonas* sp. strain SD 705 (WO 95/06720 and WO 96/27002), *P. wisconsinensis*, a *Bacillus* lipase, e.g. from *B. subtilis* (Dartois et al. (1993), Biochemica et Biophysica Acta, 1131, 253-360), *B. stearothermophilus* (JP 64/744992) or *B. pumilus* (WO 91/16422). Each document is incorporated by reference in its entirety for all purposes, but in particular the disclosure of enzyme identity, structure, reactivity and methods of obtaining said enzymes.

Commercially available mesophilic lipase enzymes include Lipolase™ and Lipolase Ultra™, Lipex™ (Novozymes NS).

Exemplary mesophilic phospholipases (EC 3.1.1.4 and/or EC 3.1.1.32) include enzymes which hydrolyse phospholipids. Phospholipases $A_1$ and $A_2$ which hydrolyze one fatty acyl group (in the sn-1 and sn-2 position, respectively) to form lysophospholipid; and lysophospholipase (or phospholipase B) which can hydrolyze the remaining fatty acyl group in lysophospholipid are included as are Phospholipase C and phospholipase D (phosphodiesterases) which release diacyl glycerol or phosphatidic acid respectively.

The term "phospholipase A" used herein in connection with an enzyme of the invention is intended to cover an enzyme with Phospholipase $A_1$ and/or Phospholipase $A_2$ activity. The phospholipase activity may be provided by enzymes having other activities as well, such as, e.g., a lipase with phospholipase activity.

The mesophilic phospholipase may be of any origin, e.g., of animal origin (such as, e.g., mammalian), e.g. from pancreas (e.g., bovine or porcine pancreas), or snake venom or bee venom. Preferably the phospholipase may be of microbial origin, e.g., from filamentous fungi, yeast or bacteria, such as the genus or species *Aspergillus*, e.g., *A. niger*; *Dictyostelium*, e.g., *D. discoideum*; *Mucor*, e.g. *M. javanicus, M. mucedo, M. subtilissimus*; *Neurospora*, e.g. *N. crassa*; *Rhizomucor*, e.g., *R. pusillus*; *Rhizopus*, e.g. *R. arrhizus, R. japonicus, R. stolonifer, Sclerotinia*, e.g., *S. libertiana*; *Trichophyton*, e.g. *T. rubrum*; *Whetzelinia*, e.g., *W. sclerotiorum*; *Bacillus*, e.g., *B. megaterium, B. subtilis*; *Citrobacter*, e.g., *C. freundii*; *Enterobacter*, e.g., *E. aerogenes, E. cloacae Edwardsiella, E. tarda*; *Erwinia*, e.g., *E. herbicola*; *Escherichia*, e.g., *E. coli*; *Klebsiella*, e.g., *K. pneumoniae*; *Proteus*, e.g., *P. vulgaris*; *Providencia*, e.g., *P. stuartii*; *Salmonella*, e.g. *S. typhimurium*; *Serratia*, e.g., *S. liquefasciens, S. marcescens*; *Shigella*, e.g., *S. flexneri*; *Streptomyces*, e.g., *S. violeceoruber*; *Yersinia*, e.g., *Y. enterocolitica*. Thus, the phospholipase may be fungal, e.g., from the class Pyrenomycetes, such as the genus *Fusarium*, such as a strain of *F. culmorum, F. heterosporum, F. solani*, or a strain of *F. oxysporum*. The phospholipase may also be from a filamentous fungus strain within the genus *Aspergillus*, such as a strain of *Aspergillus awamori, Aspergillus foetidus, Aspergillus japonicus, Aspergillus niger* or *Aspergillus oryzae*.

Preferred mesophilic phospholipases are derived from a strain of *Humicola*, especially *Humicola lanuginosa* or variant; and from strains of *Fusarium*, especially *Fusarium oxysporum*. The phospholipase may be derived from *Fusarium oxysporum* DSM 2672.

Preferably mesophilic phospholipases comprise a phospholipase A, (EC. 3.1.1.32). or a phospholipase A2 (EC.3.1.1.4.).

Examples of commercial mesophilic phospholipases include LECITASE™ and LECITASE™ ULTRA, YIELSMAX, or LIPOPAN F (available from Novozymes NS, Denmark).

Other Enzymes

Advantageously, alternatively, or additionally, the psychrophilic enzyme can comprise an esterase (ester hydrolase) such as a carboxylic ester hydrolase. For example, the enzyme can include a glycosyl hydrolase (glycosylase) for example a cellulase, an amylase (including alpha-amylases), a xylanase, etc.

Psychrophilic esterases preferably include esterases EstAT1 and EstAT11 described by Jeon et al. Mar Biotechnol (2009) 11:307-316, which is incorporated by reference in its entirety for all purposes, but in particular the disclosure of enzyme identity, structure, reactivity and methods of obtaining said enzymes.

Psychrophilic glycosyl hydrolases preferably include glycosidases such as amylases, e.g. α-amylases from *Pseudoalteromonas haloplanktis* strain TAC 125 and from *Alteromonas haloplanktis* A23 (Feller et al (1998) Journal Biological Chemistry Vol 273, No. 20 pp 12109-12115) and from *Nocardiopsis* sp. 7326; cellulases and xylanase from e.g. *Clostridium* sp. PXYL1 (G. Akila, T. S. Chandra (2003) FEMS Microbiol. Letters 219, 63-67). Psychrophilic xylanases include *E. coli* phagemid (Lee et al. 2006b). Each document is incorporated by reference in its entirety for all purposes, but in particular the disclosure of enzyme identity, structure, reactivity and methods of obtaining said enzymes.

Exemplary psychrophilic proteases include those derived from *Flavobacterium balustinum* P104 (isolated from the internal organs of salmon and has been deposited in National Institute of Bioscience and Human-Technology, Agency of Industrial Science and Technology as the deposit number of FERM BP-5006 on Feb. 17, 1995 and described in WO/1996/025489) and from *Arthrobacter globiformis* S155 (Poitier et al, (1995) J. Gen. Microbiol. 133:2797-2806). Each document is incorporated by reference in its entirety for all purposes, but in particular the disclosure of enzyme identity, structure, reactivity and methods of obtaining said enzymes.

Psychrophilic lyases preferably include pectate lyases e.g. from *Pseudoalteromonas haloplanktis* strain ANT/505 (Truong et al (2001) Extremophiles 5: 35-44). Preferably, the one or more mesophilic enzymes comprise proteases and/or glycosidases and/or pectate lyases.

Mesophilic proteases include serine protease or a metallo protease, preferably an alkaline microbial protease or a trypsin-like protease. Alkaline proteases include subtilisins, especially those derived from *Bacillus*, e.g., subtilisin Novo, subtilisin Carlsberg, subtilisin 309, subtilisin 147 and subtilisin 168. The protease may be trypsin-like (i.e. capable of cleaving peptide bonds at the C-terminal side of lysine or arginine). Such proteases may be of porcine or bovine origin. *Fusarium* derived trypsin proteases are also included.

Commercially available protease enzymes include Alcalase™, Savinase™, Primase™ Duralase™, Dyrazym™, Esperase™, Everlase™, Polarzyme™, and Kannase™ (Novozymes A/S), Maxatase™, Maxacal™, Maxapem™, Properase™, Purafect™ Purafect OxP™, FN2™, and FN3™ (Genencor International Inc.).

Exemplary mesophilic cutinases (EC 3.1.1.74.) are derived from a strain of *Aspergillus*, in particular *Aspergillus oryzae*, a strain of *Alternaria*, in particular *Alternaria brassiciola*, a strain of *Fusarium*, in particular *Fusarium solani, Fusarium solani pisi, Fusarium roseum culmorum*, or *Fusarium roseum sambucium*, a strain of *Helminthosporum*, in particular *Helminthosporum sativum*, a strain of *Humicola*, in particular *Humicola insolens*, a strain of *Pseudomonas*, in particular *Pseudomonas mendocina*, or *Pseudomonas putida*, a strain of *Rhizoctonia*, in particular *Rhizoctonia solani*, a strain of *Streptomyces*, in particular *Streptomyces scabies*, or a strain of *Ulocladium*, in particular *Ulocladium consortiale*. Most preferably cutinase is derived from a strain of *Humicola insolens*, in particular the strain *Humicola insolens* DSM 1800.

Commercial cutinases include NOVOZYM™ 51032 (available from Novozymes NS, Denmark).

Exemplary mesophilic amylases (alpha and/or beta) are included for example, alpha-amylases obtained from *Bacillus*, e.g. from strains of *B. licheniformis* NCIB8059, ATCC6634, ATCC6598, ATCC11945, ATCC 8480, ATCC9945a, or the *Bacillus* sp. strains DSM 12649 (AA560 alpha-amylase) or *Bacillus* sp. DSM 12648 (AA349 alpha-amylase).

Commercially available mesophilic amylases are Duramyl™, Termamyl™, Termamyl Ultra™, Natalase™, Stainzyme™, Fungamyl™ and BAN™ (Novozymes NS), Rapidase™ and Purastar™ (from Genencor International Inc.).

Exemplary mesophilic cellulases include cellulases from the genera *Bacillus, Pseudomonas, Humicola, Fusarium, Thielavia, Acremonium*, e.g. the fungal cellulases produced from *Humicola insolens, Thielavia terrestris, Myceliophthora thermophila*, and *Fusarium oxysporum*.

Especially preferred mesophilic cellulases are the alkaline or neutral cellulases having color care benefits. Commercially available cellulases include Celluzyme™, Carezyme™, Endolase™, Renozyme™ (Novozymes NS), Clazinase™ and Puradax HA™ (Genencor International Inc.), and KAC-500(B)™ (Kao Corporation).

Exemplary mesophilic pectate lyases include pectate lyases that are derived/cloned from bacterial genera such as *Erwinia, Pseudomonas, Klebsiella* and *Xanthomonas*, as well as from *Bacillus subtilis* (Nasser et al. (1993) FEBS Letts. 335:319-326) and *Bacillus* sp. YA-14 (Kim et al. (1994) Biosci. Biotech. Biochem. 58:947-949); *Bacillus pumilus* (Dave and Vaughn (1971) J. Bacteriol. 108:166-174), *B. polymyxa* (Nagel and Vaughn (1961) Arch. Biochem. Biophys. 93:344-352), *B. stearothermophilus* (Karbassi and Vaughn (1980) Can. J. Microbiol. 26:377-384), *Bacillus* sp. (Hasegawa and Nagel (1966) J. Food Sci. 31:838-845) and *Bacillus* sp. RK9 (Kelly and Fogarty (1978) Can. J. Microbiol. 24:1164-1172. Each document is incorporated by reference in its entirety for all purposes, but in particular the disclosure of enzyme identity, structure, reactivity and methods of obtaining said enzymes. Divalent cation-independent and/or thermostable pectate lyases may be used.

Examples of commercially available alkaline mesophilic pectate lyases include BIOPREP™ and SCOURZYME™ L from Novozymes NS, Denmark.

Exemplary mesophilic mannanases (EC 3.2.1.78) include derived from a strain of the filamentous fungus genus *Aspergillus*, preferably *Aspergillus niger* or *Aspergillus aculeatus* or *Trichoderma reseei* or from the *Bacillus* microorganism FERM P-8856 which produces beta-mannanase and beta-mannosidase or from alkalophilic *Bacillus* sp. AM-001 or from *Bacillus amyloliquefaciens*. The mannanase may comprise alkaline family 5 and 26 mannanases derived from *Bacillus agaradhaerens, Bacillus licheniformis, Bacillus halodurans, Bacillus clausii, Bacillus* sp., and *Humicola insolens*.

Examples of commercially available mannanases include Mannaway™ available from Novozymes NS Denmark.

Exemplary mesophilic peroxidases/oxidases include peroxidases from *Coprinus*, e.g. from *C. cinereus*, and variants thereof. Commercially available peroxidases include Guardzyme™ and Novozym™ 51004 (Novozymes NS).

Thermophilic Enzymes

Thermophilic proteases include proteases derived from Thermophilic *Bacillus* strain HS08 (African Journal of Biotechnology Vol. 5 (24), pp. 2433-2438, 18 Dec. 2006) and *B. Stearothermophilius* 1503; *Thermos caldophilus* GK24; *T. Aquaticus* T351; *T. aquaticus* YT1 Aq.I and Aq. II.

Thermophilic lipases include those derived from *Bacillus thermocatenulatus* BTL1 and preferably BTL2 (Schimdt-Dannert et al, *Biochim. Biophys. Acta* (1994) 1214, pp. 43-5 and *Biochim. Biophys. Acta* (1996) 1301, pp. 105-114).

Thermophilic glycosyl hydrolases include alpha-amylases from *B. stearothermophilus Donk*, strain BS-1 (Journal Biochemistry, Vol 67, 1:65-75) and from *Bacillus* sp. ANT-6 (Process Biochemistry (May 2003) Vol 38, 10:1397-1403). Thermophilic lyases include the pectate lyases from *Thermoanaerobacter italicus* sp. *nov*. strain Ab9 (Kozianowski et al., (1997) Extremophiles Vol 1, 4:171-182). Each document is incorporated by reference in its entirety for all purposes, but in particular the disclosure of enzyme identity, structure, reactivity and methods of obtaining said enzymes.

Once each suitable enzyme is chosen according to the invention, it is relatively easy for the skilled man to isolate a suitable micro-organism capable of producing the enzyme and to carry out optimization procedures known in the art for making enzymes which have the required stability/performance in e.g. powder or liquid compositions and/or in certain washing conditions etc.

Compositions

The composition may be a fabric treatment composition such as a laundry/fabric cleaning/care composition and may comprise one or more surfactants and/or optionally other ingredients.

Such compositions of the invention may be in dry solid form e.g. powdered, granules or tableted powders or liquid or gel form. It may also be in the form of a solid detergent bar. The composition may be a concentrate to be diluted, rehydrated and/or dissolved in a solvent, including water, before use. The composition may also be a ready-to-use (in-use) composition.

In some cases, the composition is a liquid formulation.

The present invention is suitable for use in industrial or domestic fabric wash compositions, fabric conditioning compositions and compositions for both washing and conditioning fabrics (so-called through the wash conditioner compositions). The present invention can also be applied to industrial or domestic non-detergent based fabric care compositions, for example direct application e.g. roll-on or spray-on compositions which may be used as a pre-treatment of e.g. localised portions of fabric prior to a 'main' wash.

The enzymes may be present at 0-5 wt %, preferably 2-4 wt %, and most preferably 2.5-3.5 wt % of the composition (where wt % means percentage of the total weight of the composition).

The total protein concentration (of the total range of enzymes according to the invention) in the wash liquor may be from 0.01 to 10.0 mg/L, for example from 2 to 5 mg/L.

Biosurfactant

The biosurfactant preferably comprises a microbially-derived biosurfactant. Preferably it comprises a glycolipid biosurfactant moiety which may be a rhamnolipid or sophorolipid or trehalolipid or a mannosylerythritol lipid (MEL) or combinations thereof.

Alternatively or additionally the biosurfactant may comprise any shear thinning biosurfactant and in this respect, may extend to include any shear thinning glycolipid biosurfactant mentioned above or any shear thinning cellobiose, peptide based biosurfactant, lipoprotein, lipopeptide e.g. surfactin, fatty acids e.g. corynomucolic acids (preferably with hydrocarbon chain $C_{12}$-$C_{14}$), phospholipid (e.g. phosphatidylethanolamine produced by *Rhodococcus erythropolis* grown on n-alkane resulted in the lowering of interfacial tension between water and hexadecane to less than 1 mN $m^{-1}$ and CMC of 30 mg $L^{-1}$ (Kretschner et al., 1982)), spiculisporic acid, polymeric biosurfactants including emulsan, liposan, mannoprotein or polysaccharide-protein complexes or combinations thereof.

The biosurfactant moiety may comprise one or more saccharide moieties such as sugar rings.

In some cases the biosurfactant is a mannosylerythritol lipid (MEL):

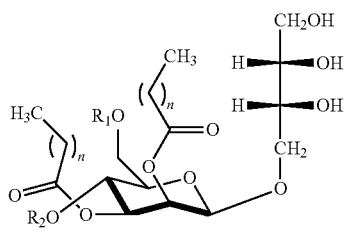

MEL-A: $R_1=R_2=Ac$; MEL-B: $R_1=Ac$, $R_2=H$; MEL-C: $R_1=H$; $R_2=Ac$: n=6-10.

In some cases, the biosurfactant is MEL-B.

In some cases, the biosurfactant moiety comprises a rhamnolipid.

In the case of rhamnolipids the rhamnolipid may comprise one or two sugar ring: mono-rhamnolipids having a single rhamnose sugar ring and di-rhamnolipids, having two rhamnose sugar rings.

In the case of rhamnolipids, throughout this patent specification, the prefixes mono- and di- are used to indicate respectively to indicate mono-rhamnolipids (having a single rhamnose sugar ring) and di-rhamnolipids (having two rhamnose sugar rings) respectively. If abbreviations are used R1 is mono-rhamnolipid and R2 is di-rhamnolipid.

The ratio of enzyme to biosurfactant surfactant may, for example, be from 1:0.5 to 1:20, preferably from 1:0.5 to 1:10, such as from 1:0.5 to 1:5.

The biosurfactant can be used to replace at least 50 wt. % of a total surfactant in the composition. In some cases, the stated biosurfactant is the only biosurfactant present.

Preferably the biosurfactant is present at a level of 20-90 wt. % of the total surfactant and more preferably the biosurfactant is present at 50-80 wt. % of the total surfactant and more preferably 50-75% wt. % of the total surfactant.

Other Ingredients

The enzymes may be the sole fabric treatment agent or other stain removal agents may be incorporated.

Other detergent ingredients may be included including surfactants, builders, sequestering agents, hydrotropes, preservatives, complexing agents, polymers, stabilizers, perfumes, optical brighteners, or other ingredients such as e.g. fabric conditioners including clays, foam boosters, suds suppressors (anti-foams), anti-corrosion agents, soil-suspending agents, anti-soil redeposition agents, anti-microbials, tarnish inhibitors, or combinations of one or more thereof, provided that these ingredients are compatible with the enzymes.

The fabric wash compositions may comprise a fabric wash detergent material selected from non-soap anionic surfactant, nonionic surfactants, soap, amphoteric surfactants, zwitterionic surfactants and mixtures thereof.

It will be appreciated that the composition may include both biosurfactants and non-biosurfactants (in other words, a fabric wash detergent material, termed for ease a non-biosurfactant, and a biosurfactant.

Any enzyme present in a composition may be stabilized using conventional stabilizing agents, e.g., a polyol such as propylene glycol or glycerol, a sugar or sugar alcohol, lactic acid, boric acid, or a boric acid derivative, e.g., an aromatic borate ester, or a phenyl boronic acid derivative such as 4-formylphenyl boronic acid.

The following examples are provided by way of illustration and not by way of limitation.

EXPERIMENTAL (I) *Psychromonas* Ingrahami Lipase

Cloning & Expression Including Sequence Information

A putative class 3 lipase from *P. ingrahamii* gene (PinLip) was identified used BLASTp. The PinLip protein sequence was searched against structural characterised proteins in the PDB and showed highest homology to Lipex from *Rhizomucor miehei* (*Mucor miehei* PDB: 5TGL) and Lipex (1TIB) with sequence identify of 14% to both. Protein sequence alignment of PinLip to Lipex allowed the identification of Ser and Asp (FIG. 1 serine and aspartate are conserved and identified in the sequence alignment, shown by underline) in the catalytic triad but the third residue in the triad could not be identified because of very low sequence identity in the C-terminal region of the lipases. Sequence alignments also allowed the identification of the PinLip lipase lid region has also been identified (FIG. 1).

The gene coding for the PinLip into the pLATE 31 vector and successfully expressed in *E. coli* BL21 cells. Different expression conditions have been tested. An exemplary protocol is as follows: 1 L LB media supplemented with 100 $\mu gml^{-1}$ ampicillin was inoculated and incubated for 4 h at 37° C. with shaking at 180 rpm. When the OD reached 0.6 protein production was induced by the addiction of 1.0 mM IPTG. Cultures were further incubated at 22° C. for 24 h with shaking at 180 rpm. After this time the cells were harvested by centrifugation at 5000 g for 30 minutes at 4° C. The cell pellet was resuspended in 50 mM Tris-HCl pH 9.5 with 1 mM $CaCl_2$ and the cells were harvested by centrifugation at 5000 g for 30 minutes at 4° C. The cell pellet was stored at −20° C. until use.

Fermentation (Harvest) & Purification

The harvested cells were resuspended in 50 mM Tris-HCl pH 9.5 with 1 mM $CaCl_2$ and 1M NaCl (Buffer A) using 5 ml/g of cells. [The selection of pH at 9.5 was based on the fact that the theoretical isoelectric point (pI) of the PinLip (pI=7.21) was below this pH value and therefore the protein would have a net negative charge at this pH value.] Lysozyme was added to the cells suspension at a final concentration of 0.1 mg/mL and the suspension was stirred for 1 h at 4° C. The suspension was then sonicated using ten bursts of 20 seconds each with one minute rest on ice between bursts. The lysate was then centrifuged at 24000 rpm for 1 h at 4° C. and the supernatant collected.

Purification by Hydrophobic Interaction (HIC) The supernatant was loaded on Butyl FF column (size 1 mL). The column was previously equilibrated with 5 volume of Buffer A and the protein was eluted with a linear gradient between Buffer A and 50 mM Tris-HCl pH 9.5 with 1 mM $CaCl_2$ (Buffer B). All eluted fractions were run on a SDS-PAGE gel. The fractions showing highest content of PinLip were pooled and concentrated. The protein was loaded on a DEAE FF column (size 1 mL) previously equilibrated with 5 volume of Buffer B and the protein was eluted with a linear gradient between Buffer B and Buffer A. The fractions containing the pure PinLip were pooled and assayed for lipase activity.

As an alternative to the two-step purification procedure of HIC followed by DEAE, a one-step procedure based on a two-column tandem affinity setting (maltose binding protein plus immobilized metal ion affinity chromatography for His-tagged PinLip) has been successfully applied. The purity of the final PinLip sample may be higher compared to the two column purified product (data not shown).

Bioanalytics

SDS-PAGE was performed using a Bio-Rad Protean apparatus. The protein samples were initially boiled for 10 min at 100° C. after being diluted with Laemli loading buffer in order to denature the protein. Samples were then cooled and loaded on 10% acrylamide gel. Separation was performed in a running buffer following the running conditions: 120V, 400 mA, for 90 min at room temperature. Protein bands on SDS-PAGE gels were revealed by staining in "Comassie blue" prepared following the manufacturer's protocol. De-staining was performed at room temperature for 30 minutes to remove the excess dye. Results are shown in FIG. 2. The estimated purification yield is 5 mg/L.

Lipase Assay

Figure 3:
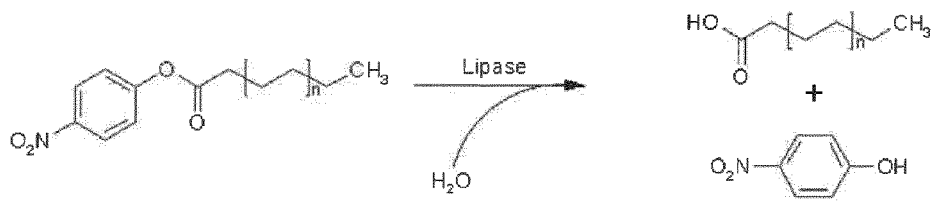
FIG. 3 shows a schematic reaction of pNp-ester hydrolysis performed by a lipase.
Figure 4:
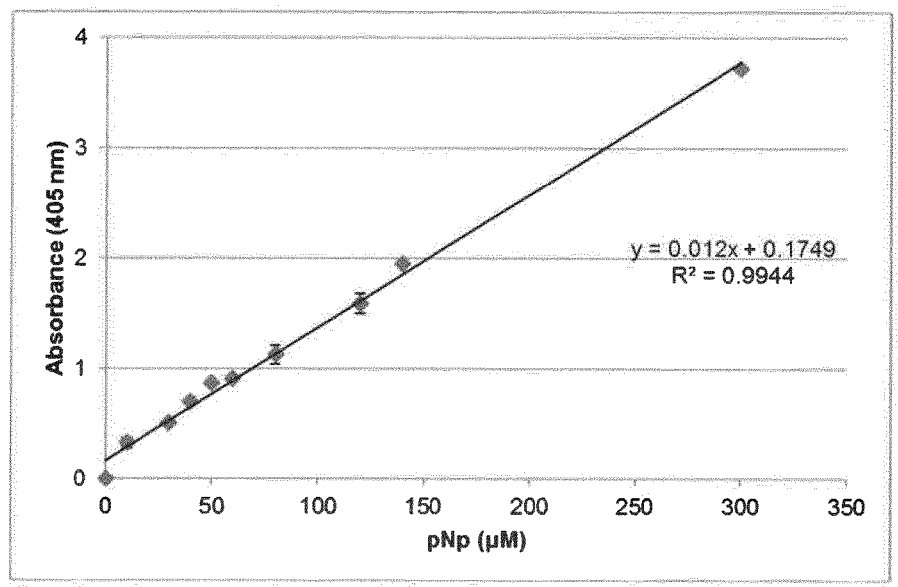
FIG. 4 shows linearisation of pNp calibration curve.

For activity evaluation an assay based on the pNp release was performed (FIG. 3). Lipase was assayed in quadruplicate in a 96-well microtiter plate using p-nitrophenyllaurate (Sigma-Aldrich) as the substrate. 20 µL of PinLip (final concentration in well 25 ng/ml) was mixed with 100 µL of 50 mM Tris-HCl pH 8.5 containing 1 mM $CaCl_2$, and 0.01% of AOS plus 60 µL of water and 20 µL of 1 mM pNp laurate. After 15 min of incubation at different temperature, the OD 410 was measured against an enzyme-free control. The values obtained have been calculated as µM of pNp released using the standard curve shown in FIG. 4.

Results

Figure 5A:
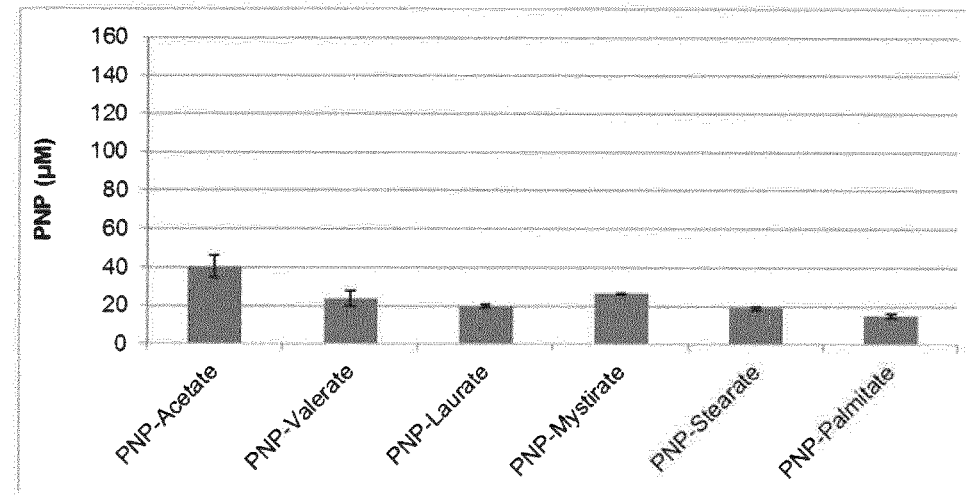
FIG. 5 shows PinLip activity towards different pNp-esters at: 5a: 4° C.; 5b:15° C.; 5c: 25° C.
Figure 5B:
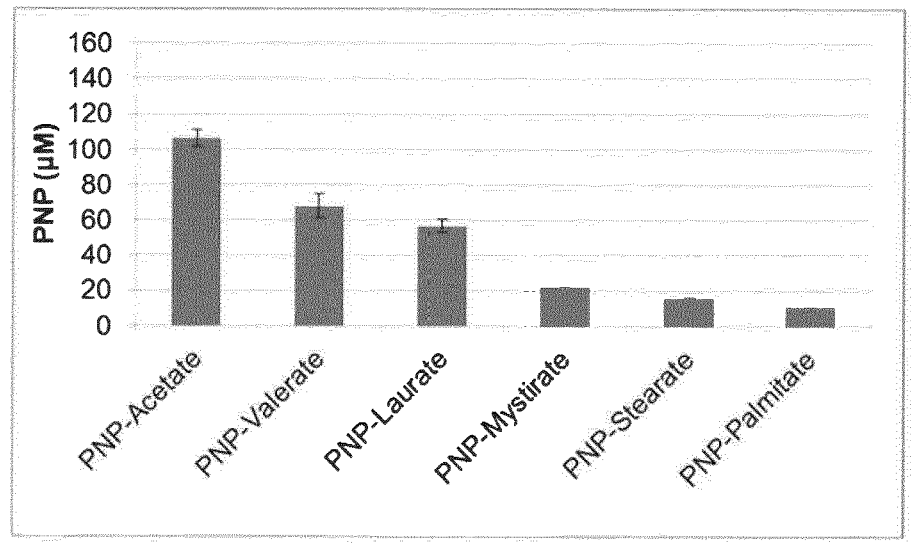
Figure 5C:
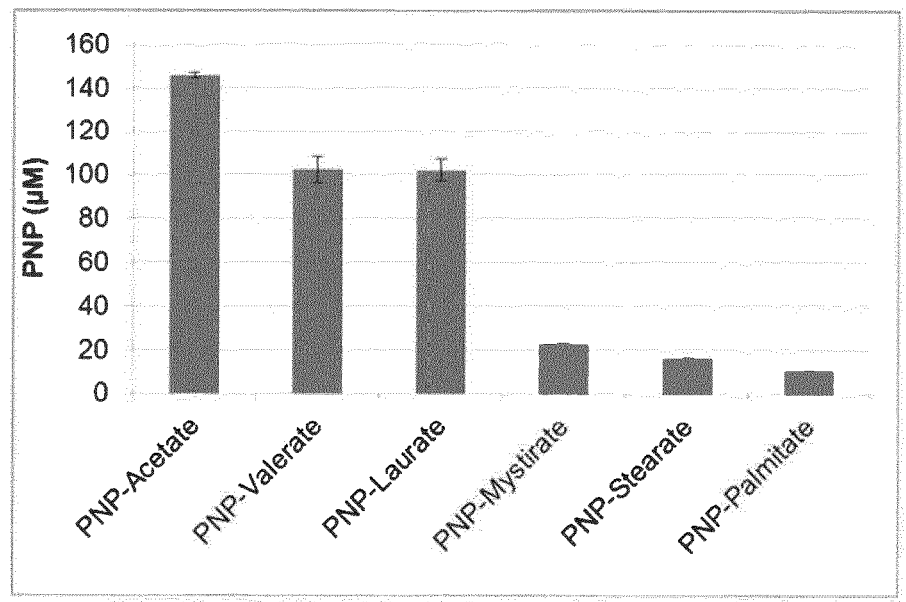

The results of the lipase assay are shown in FIG. 5. FIG. 5 shows that the PinLip is active towards a wide range of pNp-ester covering different chain lengths and also that the increasing of temperature lead to an improved activity towards short/medium length esters.

End-Point Stain Removal Assays

The following soiled cloth samples were hole-punched into discs and transferred to 300 µl 96 well plates:

Lipase sensitive stains: CS61—Beef fat stain and C646B—Used fry fat (CFT BV)

Laundry Enzymes (Novozymes):

Lipex 100 L (Novozymes)

T. lanuginosa lipase (Sigma-Aldrich)

Enzyme

Psychromonas ingrahamii Lipase (PinLip)

Procedure:

Test Mixture: Total wash volume=200 µl

Soluble enzyme PinLip/Lipex (20 mg/L in assay well)=20 µl

Blackbull formulation 8 g/L stock (0.8 g/L final in assay well)=20 µl

Prenton Water=160 µl

In both cases the enzyme was added last. Two sets of reactions were incubated at 20 and 40 degrees respectively for 1 hour with shaking at 250 rpm.

The assay plates were dried overnight.

After drying, the stain plates were digitally scanned and their deltaE measured. This value is used to express cleaning effect and is defined as the colour difference between a white cloth and that of the stained cloth after being washed. Mathematically, the definition of deltaE is:

$$\mathrm{delta}E = [(\Delta_L)^2 + (\Delta_a)^2 + (\Delta_b)^2]^{1/2}$$

wherein $\Delta_L$ is a measure of the difference in darkness between the washed and white cloth; $\Delta_a$ and $\Delta_b$ are measures for the difference in redness and yellowness respectively between both cloths. From this equation, it is clear that the lower the value of deltaE, the whiter the cloth will be. With regard to this colour measurement technique, reference is made to Commission International de l'Eclairage (CIE); Recommendation on Uniform Colour Spaces, colour difference equations, psychometric colour terms, supplement no. 2 to CIE Publication, no. 15, Colormetry, Bureau Central de la CIE, Paris 1978.

Results

Figure 6:
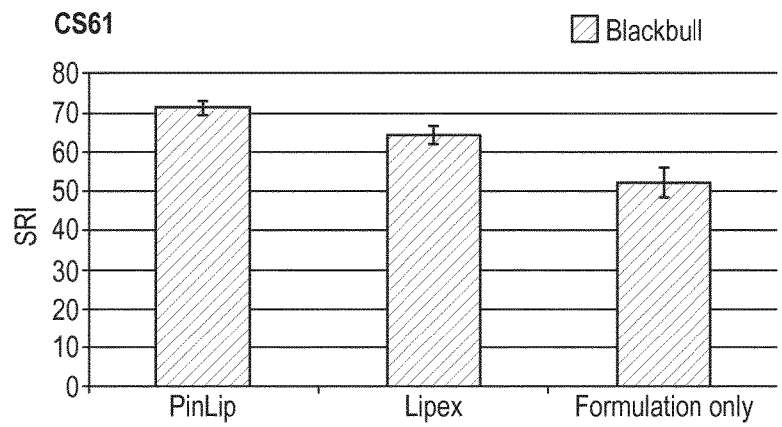
FIG. 6 shows a comparison of PinLip and Lipex in combination with a formulation (Blackbull), and the control of the formulation alone.

In FIG. 6 the cleaning effect is expressed in the form of a stain removal index (SRI): SRI=100−deltaE. The higher the SRI the cleaner the cloth, SRI=100 (white). PinLip shows a better cleaning effect compared to Lipex in high (~30%) and low total surfactancy (~15%).

Dose Dependant Wash Study

Figure 7A:
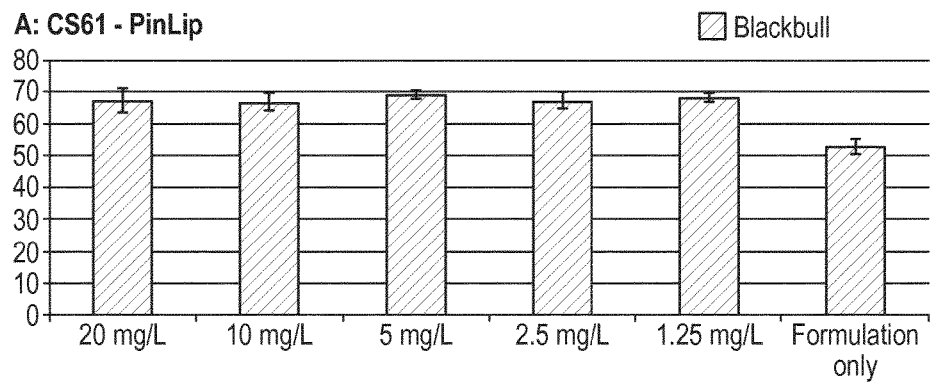
FIG. 7 shows SRI values at a variety of enzyme concentrations for both PinLip (a) and Lipex (b).
Figure 7B:
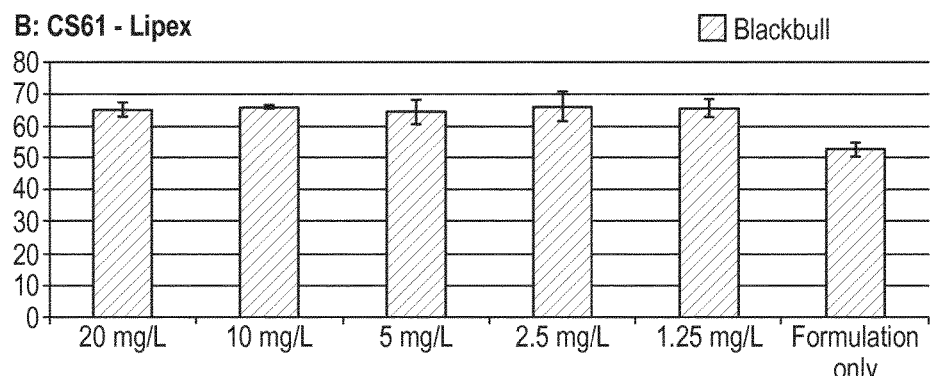

As further investigation the same end point wash studies has been conducted varying the concentration of enzyme in order to find the best dosage (FIG. 7). These results show that PinLip is superior in cleaning compared to benchmark Lipex at different enzyme doses used, especially in the range between 20 and 2.5 mg/L.

Impact of Rhamnolipids on Enzymatic Cleaning (No Formulation)

In order to understand the effect of rhamnolipids on cleaning effect of enzymes, different rhamnolipids i.e. R1 (mono rhamnolipid), 4R2 (di rhamnolipid) and MEL-B (Mannnosylerythritol lipid B), 1614 Mel (multi-MEL components) were screened at different concentration levels in presence and absence of enzymes in wash study. A stock concentration of 70% (active) rhamnolipid was prepared for wash study and diluted using mili-Q water to achieve a working stock concentration in range of 20% to 1.25%. Wash study was carried out in similar way as mentioned in above sections.

Test Mixture: Total wash volume=200 µl

Soluble enzyme PinLip/Lipex (20 mg/L in assay well)=20 µl

Rhamnolipid 8 g/L stock (0.8 g/L final in assay well)=20 µl

Prenton Water=160 µl

In both cases the enzyme was added last. Assay plates were incubated at 20 degrees for 1 hour with shaking at 250 rpm.

4R2 RL increases its cleaning performance on its own with increasing concentration, so that the contribution from the enzymes is minimal above 0.05% 4R2 RL. In 4R2 RL, PinLip and Lipex showed equivalent good cleaning performance in the presence of R2, even better at low RL concentration.

Figure 8A:
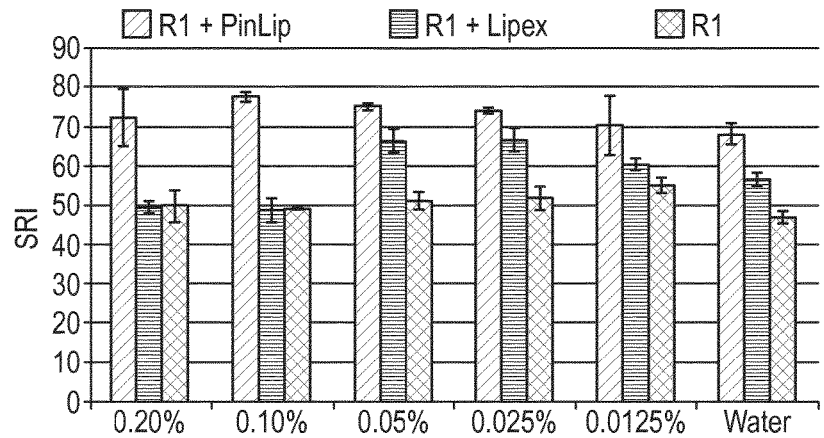
FIG. 8 shows the SRI values for PinLip in combination with various biosurfactants at differing concentrations of biosurfactant.

In R1 RL, PinLip shows better synergistic cleaning performance (enzyme plus RL) than the benchmark enzyme, Lipex. See FIG. 8a.

Figure 8B:
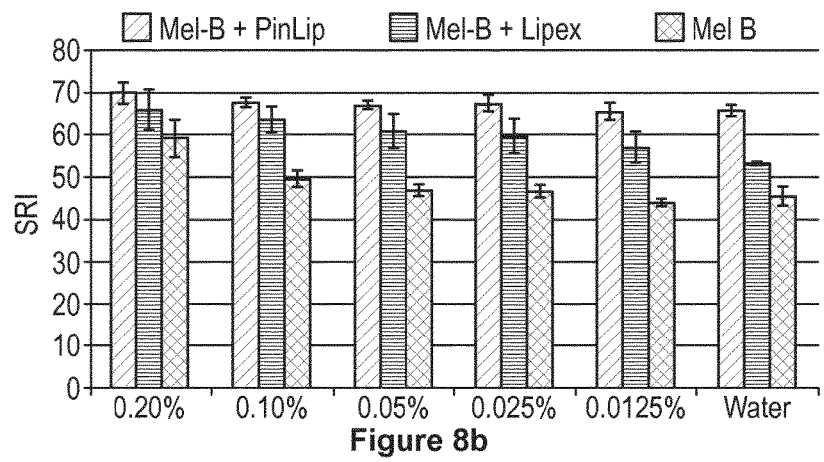
Figure 8C:
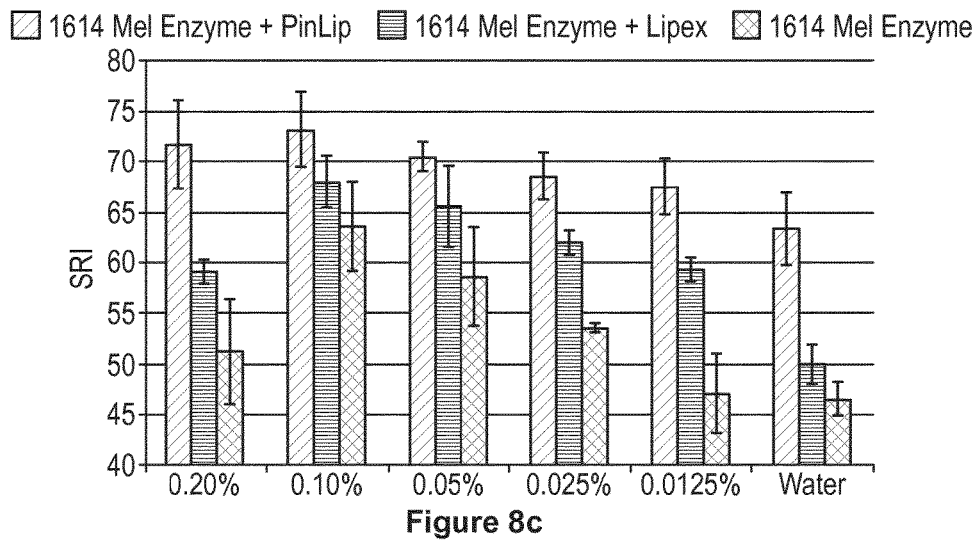

In presence of 1614 MEL and MEL-B in combination with PinLip showed over the full dosage range superior cleaning compared to the MEL Lipex combination. See FIGS. 8b and 8c.

Partial Detergency Substitution in Formulation by RL

In order to study the effect of rhamnolipid in presence of LAS/SLES/NI on cleaning effect of lipases, a range of formulations were prepared by adding rhamnolipids at different concentration level in presence of LAS, SLES, and NI. The ratio of LAS, SLES, and NI was 2:1:3 in the prepared formulations. The wash study was carried out as mentioned in above section.

TABLE 1

Formulation containing different level of biosurfactant (rhamnolipids) and chemical surfactant to give 100% active surfactant system. In given chemical surfactant system the ratio of LAS, SLES and NI was 2:1:3.

| Biosurfactant (%) | Surfactant (LAS:SLES:NI) (2:1:3)(%) | Total |
|---|---|---|
| 10 | 90 | 100 |
| 20 | 80 | 100 |
| 30 | 70 | 100 |
| 40 | 60 | 100 |
| 50 | 50 | 100 |

TABLE 2

Amounts of various components in the biosurfactant and surfactant blend.

| Bio-surfactant (g) | LAS (g) | SLES (g) | NI (g) | Total (g) in 1000 ml |
|---|---|---|---|---|
| 0.8 | 2.4 | 1.2 | 3.60 | 8 |
| 1.6 | 2.13 | 1.07 | 3.20 | 8 |
| 2.4 | 1.87 | 0.93 | 2.80 | 8 |
| 3.2 | 1.60 | 0.80 | 2.40 | 8 |
| 4   | 1.33 | 0.67 | 2.00 | 8 |

Figure 9A:
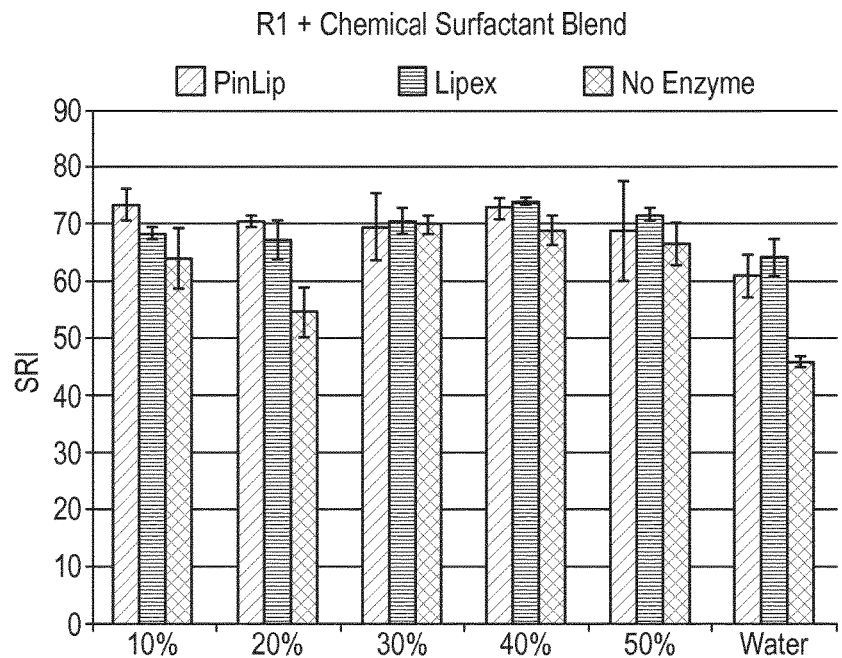
FIG. 9 shows SRI values for varying ratios of biosurfactant to surfactant.

Rhamnolipids (R1—one rhamnose molecule, 4R2—two rhamnose molecules containing), and lipases were tested at a c dose in end point removal assay using CS61 Beef fat stain. 8 replicates were performed in parallel on the same 96 well plate. The experiment was carried out at 20 degrees. The plates were scanned and the SRI values calculated. The results are shown in FIG. 9a as a bar chart displaying the average SRI for replicates. Error bars display standard deviation between the replicates for each condition.

In a R1 modified chemical surfactant blend, PinLip shows better cleaning than Lipex up to 30% R1 content in the formulation (strong positive impact at low concentration in formulation).

Figure 9B:
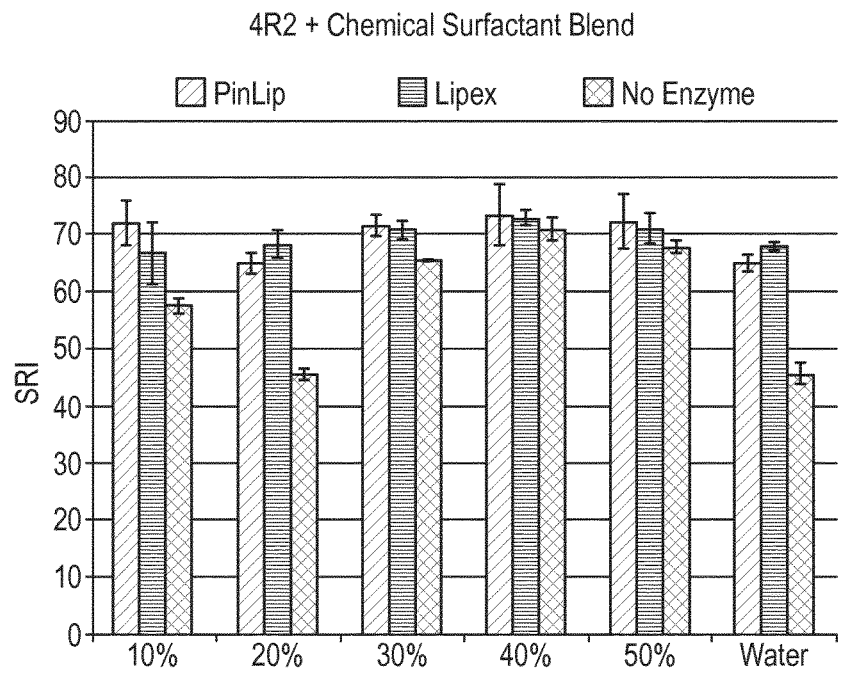

In a R2 modified chemical surfactant blend, the results revealed that PinLip shows better cleaning than Lipex below 20% R2 content, at higher content of R2, Lipex and PinLip showed parity in cleaning and above 30% not better any more than the modified formulation. The results are shown in FIG. 9b as a bar chart displaying the average SRI for replicates. Once again, error bars display standard deviation between the replicates for each condition.

The invention claimed is:

1. A composition comprising *Psychromonas ingrahamii* lipase and a biosurfactant selected from a rhamnolipid, sophorolipid, trehalolipid, a mannosylerythritol lipid (MEL), and combinations thereof.

2. The composition of claim 1, wherein the biosurfactant is a rhamnolipid, optionally wherein the rhamnolipid comprises at least 50 wt. % monorhamnolipid, optionally wherein the rhamnolipid comprises at least 80 wt. % monorhamnolipid.

3. The composition of claim 1, wherein the biosurfactant is a mannosylerythritol lipid, optionally wherein the mannosylerythritol lipid comprises at least 50 wt. % mannosylerythritol lipid B, optionally wherein the mannosylerythritol lipid comprises at least 80 wt. % mannosylerythritol lipid B.

4. The composition of claim 1, wherein the biosurfactant content of the composition is 30 wt. % or less.

5. The composition of claim 1, wherein the ratio of biosurfactant to non-biosurfactant is from 1:9 to 1:1.

6. The composition of claim 1, wherein the ratio of *Psychromonas ingrahamii* lipase to biosurfactant is from 1:10 to 1:200, optionally wherein the ratio of *Psychromonas ingrahamii* lipase to biosurfactant is from 1:20 to 1:60.

7. A method of laundering articles, the method comprising washing articles in an aqueous wash liquor containing a composition according to claim 1, wherein the temperature of the wash liquor is 25° C. or less.

8. The method of claim 7, wherein the temperature of the wash liquor is 15-25° C.

9. The method of claim 7, wherein the concentration of *Psychromonas ingrahamii* lipase in the wash liquor is 2.5 to 20 mg/L.

10. The method of claim 7, wherein the concentration of biosurfactant in the wash liquor is 0.001 to 1 wt. %, optionally wherein the concentration of biosurfactant in the wash liquor is 0.01 to 0.2 wt %.

* * * * *

SEQUENCE LISTING

<160> NUMBER OF SEQ ID NOS: 2

<210> SEQ ID NO 1
<211> LENGTH: 269
<212> TYPE: PRT
<213> ORGANISM: Thermomyces Lanuginosa

<400> SEQUENCE: 1

```
Glu Val Ser Gln Asp Leu Phe Asn Gln Phe Asn Leu Phe Ala Gln Tyr
1               5                   10                  15

Ser Ala Ala Ala Tyr Cys Gly Lys Asn Asn Asp Ala Pro Ala Gly Thr
            20                  25                  30

Asn Ile Thr Cys Thr Gly Asn Ala Cys Pro Glu Val Glu Lys Ala Asp
        35                  40                  45

Ala Thr Phe Leu Tyr Ser Phe Glu Asp Ser Gly Val Gly Asp Val Thr
    50                  55                  60

Gly Phe Leu Ala Leu Asp Asn Thr Asn Lys Leu Ile Val Leu Ser Phe
65                  70                  75                  80

Arg Gly Ser Arg Ser Ile Glu Asn Trp Ile Gly Asn Leu Asn Phe Asp
                85                  90                  95

Leu Lys Glu Ile Asn Asp Ile Cys Ser Gly Cys Arg Gly His Asp Gly
            100                 105                 110

Phe Thr Ser Ser Trp Arg Ser Val Ala Asp Thr Leu Arg Gln Lys Val
        115                 120                 125

Glu Asp Ala Val Arg Glu His Pro Asp Tyr Arg Val Val Phe Thr Gly
    130                 135                 140

His Ser Leu Gly Gly Ala Leu Ala Thr Val Ala Gly Ala Asp Leu Arg
145                 150                 155                 160
```

```
Gly Asn Gly Tyr Asp Ile Asp Val Phe Ser Tyr Gly Ala Pro Arg Val
            165                 170                 175

Gly Asn Arg Ala Phe Ala Glu Phe Leu Thr Val Gln Thr Gly Gly Thr
        180                 185                 190

Leu Tyr Arg Ile Thr His Thr Asn Asp Ile Val Pro Arg Leu Pro Pro
            195                 200                 205

Arg Glu Phe Gly Tyr Ser His Ser Ser Pro Glu Tyr Trp Ile Lys Ser
210                 215                 220

Gly Thr Leu Val Pro Val Thr Arg Asn Asp Ile Val Lys Ile Glu Gly
225                 230                 235                 240

Ile Asp Ala Thr Gly Gly Asn Asn Gln Pro Asn Ile Pro Asp Ile Pro
                245                 250                 255

Ala His Leu Trp Tyr Phe Gly Leu Ile Gly Thr Cys Leu
            260                 265
```

<210> SEQ ID NO 2
<211> LENGTH: 378
<212> TYPE: PRT
<213> ORGANISM: Psychromonas ingrahami

<400> SEQUENCE: 2

```
Met Pro His Lys Phe Thr Met Asp His Ser Leu Leu Glu Pro Pro Ile
1               5                   10                  15

Lys Arg Ala Ala Tyr Ser Asp Arg Thr Ala Trp Leu Met Ala Val Met
            20                  25                  30

Ser Ser Leu Ala Tyr Ile Arg Phe Glu Gln Pro Thr Pro Leu Asp Glu
        35                  40                  45

Leu Ala Lys Val Leu Ser Arg Glu Thr Asn Glu Arg Asn Ile Leu Thr
    50                  55                  60

Lys Leu Asn Ala Leu Leu Ala Ala Glu Asn Arg Asp Gln Leu Lys Lys
65                  70                  75                  80

Glu Leu Lys Ser Asp Leu Gln Asp Ile Gly Phe Glu Leu Val Asp Thr
                85                  90                  95

Tyr Asn Ile Ser Ile Pro Leu Val Val Asp Thr Gln Ala Tyr Leu Ala
            100                 105                 110

Lys Ile Thr Leu Gln Asp Arg Asp Pro Met Leu Val Leu Ala Phe Arg
        115                 120                 125

Gly Thr Glu Val Thr Asn Ala Ala Asp Ile Arg Ser Asp Val Ser Ala
    130                 135                 140

Asn Pro Met Asn Ile Gly Pro Lys Glu Glu Gly His Gln Val His Ser
145                 150                 155                 160

Gly Phe Tyr Asn Ala Phe Lys Ala Ala Gln Ser Val Ile Glu Leu Ser
                165                 170                 175

Leu Asn Lys Pro Glu Leu Lys Asn Met Pro Leu Tyr Ile Thr Gly His
            180                 185                 190

Ser Leu Gly Gly Ala Leu Ala Val Val Ala Thr Tyr Cys Ile Ser Asn
        195                 200                 205

Asp Ser Val Gly Ala Cys Tyr Thr Phe Gly Gly Pro Arg Val Gly Asn
    210                 215                 220

Met Leu Phe Gly Gln Ser Ile Arg Thr Pro Val Tyr Arg Val Ile Asn
225                 230                 235                 240

Ala Ala Asp Leu Val Pro Arg Leu Pro Pro Ser Tyr Leu Ile Glu Gly
                245                 250                 255

Ile Thr Leu Leu Leu Arg Trp Leu Pro Ile Ile Pro Tyr Asn Asn Gln
            260                 265                 270
```

-continued

```
Val Ala Asp Tyr Leu Glu Arg Phe Arg His Tyr Arg His Tyr Gly Asp
        275                 280                 285

Leu Arg Tyr Leu Thr Asp Ala Thr Arg Ser Thr Pro Glu Gly Glu Gly
    290                 295                 300

Met Leu Ala Ala Tyr Pro Gly Leu Gln Val Ile Ala Asn Pro Cys Gln
305                 310                 315                 320

Leu Ser Arg Trp Ile Trp Leu Cys Ser Arg Leu Ile Ala Thr Tyr Gly
            325                 330                 335

Arg Ala Gly Ile Asn Asp His Ser Ile Asp Ile Tyr Val Glu Lys Leu
            340                 345                 350

Ala Tyr Trp Gly Ile Gln Arg Asn Leu Gly Lys Pro Lys Leu Val Ser
        355                 360                 365

Ala Gln Ala Glu Thr Lys Gly Ser Thr Gln
    370                 375
```